(12) United States Patent
Vresh et al.

(10) Patent No.: US 7,080,769 B2
(45) Date of Patent: Jul. 25, 2006

(54) LUMINAL ANASTOMOTIC DEVICE

(76) Inventors: Susan E. Vresh, P.O. Box 127, Fannettsburg, PA (US) 17221-0127; Blynn L. Shideler, 1940 Lake Marshall Dr., Gibsonia, PA (US) 15044; Krisanne Shideler, 1940 Lake Marshall Dr., Gibsonia, PA (US) 15044; Kevin S. Vresh, P.O. Box 127, Fannettsburg, PA (US) 17221-0127

( * ) Notice: Subject to any disclaimer, the term of this patent is extended or adjusted under 35 U.S.C. 154(b) by 0 days.

(21) Appl. No.: 10/910,777

(22) Filed: Aug. 2, 2004

(65) Prior Publication Data

US 2005/0067454 A1      Mar. 31, 2005

Related U.S. Application Data

(63) Continuation of application No. 10/114,421, filed on Apr. 2, 2002, now Pat. No. 6,769,590.

(60) Provisional application No. 60/280,785, filed on Apr. 2, 2001.

(51) Int. Cl.
   *B31B 1/00*    (2006.01)
   *A61B 17/04*   (2006.01)

(52) U.S. Cl. ............... 227/176.1; 227/19; 227/181.1

(58) Field of Classification Search ............ 227/19, 227/120, 110, 155, 175.1, 176.1, 180.1, 181; 411/21, 24; 606/8, 151, 153
See application file for complete search history.

(56) References Cited

U.S. PATENT DOCUMENTS

| | | | |
|---|---|---|---|
| 4,505,414 A | | 3/1985 | Filipi |
| 4,700,703 A | * | 10/1987 | Resnick et al. ........... 227/176.1 |
| 4,752,024 A | | 6/1988 | Green et al. |
| 5,219,111 A | | 6/1993 | Bilotti et al. |
| 5,669,918 A | | 9/1997 | Balazs et al. |
| 5,732,872 A | | 3/1998 | Bolduc et al. |
| 5,855,312 A | | 1/1999 | Toledano |
| 5,951,576 A | | 9/1999 | Wakabayashi |
| 6,117,148 A | | 9/2000 | Ravo et al. |
| 6,503,259 B1 | | 1/2003 | Huxel et al. |
| 6,569,173 B1 | | 5/2003 | Blatter et al. |
| 6,736,825 B1 | | 5/2004 | Blatter et al. |
| 6,769,590 B1 | | 8/2004 | Vresh et al. |
| 2002/0058955 A1 | | 5/2002 | Blatter et al. |
| 2002/0185517 A1 | | 12/2002 | Vresh et al. |

* cited by examiner

*Primary Examiner*—Scott A. Smith
*Assistant Examiner*—Brian Nash
(74) *Attorney, Agent, or Firm*—Blynn L. Shideler; Krisanne Shideler; BLK Law Group

(57) ABSTRACT

An end to end anastomotic stapling device connects two lumen sections avoiding constriction at the anastomotic ring. An intraluminal end to end anastomotic stapler includes an expanding head and anvil designed to fire an anastomotic ring having an inner diameter at least equal to the nominal inner diameter of the remaining lumen sections. An extraluminal end to end lumen stapler is described attaching the lumen sections with an exterior flange type connection having anastomotic rings with a diameter larger than the inner diameter of the lumen sections whereby the anastomotic site has a diameter at least as great as the adjacent lumen sections.

8 Claims, 12 Drawing Sheets

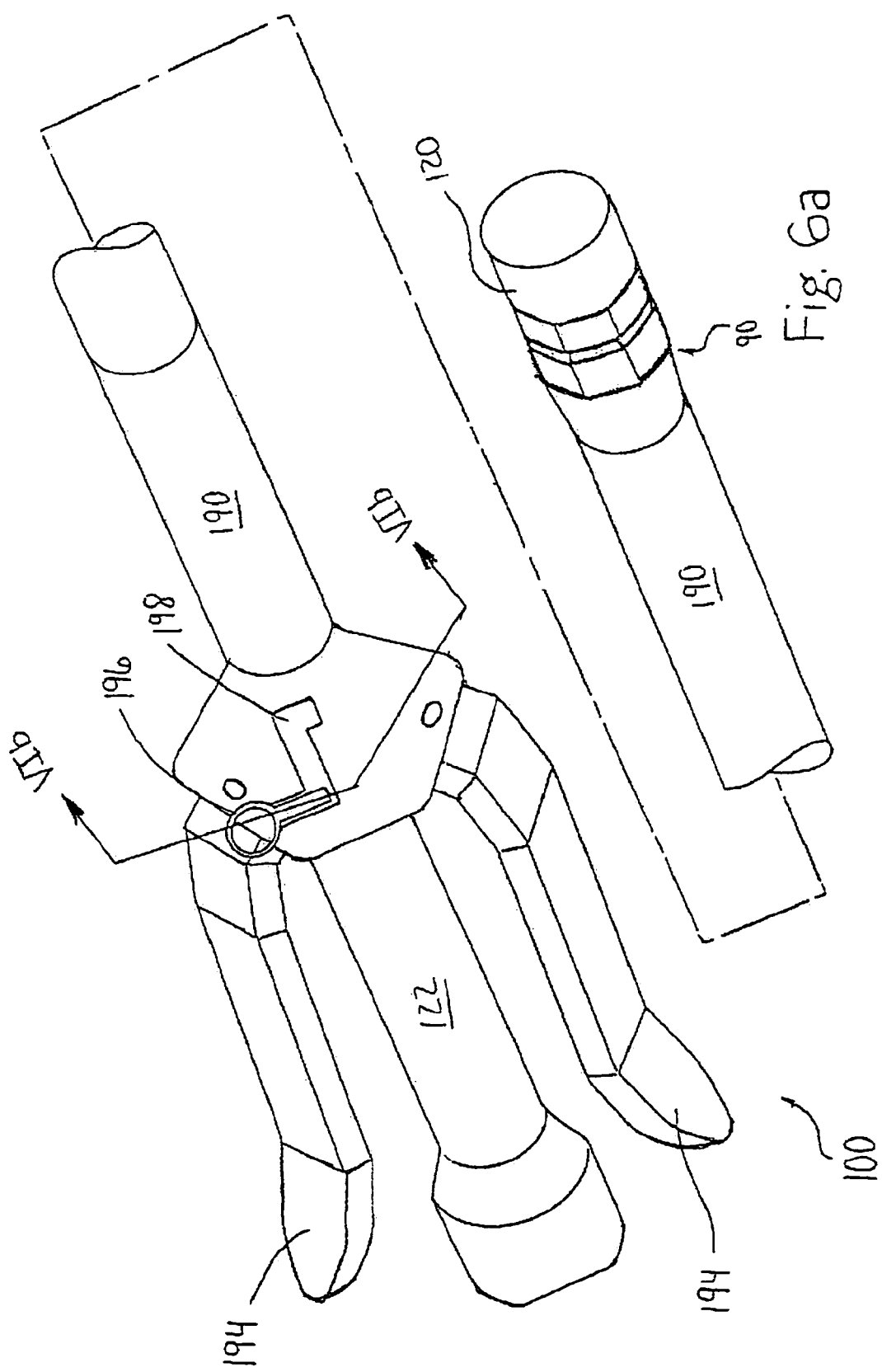

LUMINAL ANASTOMOTIC DEVICE

CROSS-REFERENCE TO RELATED APPLICATION

This application is a continuation of and claims the benefit of U.S. patent application Ser. No. 10/114,421, filed on Apr. 2, 2002 and entitled "Luminal Anastomotic Device and Method", now U.S. Pat. No. 6,769,590 which claimed the benefit of Provisional Patent Application Ser. No. 60/280,785 entitled, "Luminal Anastomotic Device and Method" filed Apr. 2, 2001. Both applications are incorporated herein by reference in their entirety.

BACKGROUND OF THE INVENTION

1. Field of the Invention

The present invention relates to surgical anastomotic stapling devices. More particularly, the present invention relates to end to end anastomotic surgical staplers avoiding minimal constrictive area at the anastomosis site.

2. Background Information

Surgical staplers have been developed to assist and improve a wide variety of surgical procedures. Surgical staplers provide precision in the placement of staples as well as decrease the time of given surgical procedures. A wide variety of surgical staplers have been developed for vascular, gastric, esophageal and intestinal surgery, to name but a few. These known staplers are often used in anastomosis procedures. In performing surgical anastomotic stapling, generally the two pieces of lumen are attached by a ring of staples with a closed loop stapler. The anastomosis of the lumen may be performed in a side to side, side to end or end to end manner which describes the relative orientation of the lumen sections.

The surgical staplers for performing end to end anastomosis are generally intraluminal surgical staplers that fire a pair of staggered rings of staples. These types of surgical staplers are often referred to as EEA's, which stands for "End to End Anastomosis". During this procedure, a circular knife blade is used to separate tissue which is held within the circular ring. The separated tissue is then removed with the stapler so that a circular opening within the lumen is completed along the surgical stapling line.

In performing these surgical procedures with EEA's it has become desirable to separate the anvil on which the staplers are clinched from the stapling head portion from which the staples are expelled. It has been typical in the past that the stapling head is attached to the anvil and the tissue is secured through a "purse stringed" gathering of tissue.

Generally, the tissue stapled together with an EEA leaves a smaller opening than the original lumen into which the anvil and stapler head were inserted. Frequently, it is desirable to provide an anvil which can be collapsed to introduce the anvil into the body through a relatively small incision. An example of a surgical stapler having a variable diameter anvil is illustrated in U.S. Pat. No. 4,505,414 disclosing an anvil, integral with a surgical stapler, which can be collapsed and inserted through a small incision in a patient's body and expanded outwardly after placement inside the patients body to staple the wall of an organ to the abdominal wall or an external tissue layer of the patient's body. The anvil is not detachable from the stapler and thus cannot provide a continuous stapler line, but rather applies a broken, discontinuous line to "tack" the tissue in a circular line. This patent also does not provide an anvil which can be placed remotely within the body for subsequent attachment to a stapler head.

Other examples of anvils which are capable of collapsing to a reduced diameter after stapling to facilitate removal from the body are shown in U.S. Pat. Nos. 4,752,024; 4,893,622; 4,700,703 and 4,903,697. These anvils are introduced into the body through a relatively large incision.

U.S. Pat. No. 5,239,639 also shows a collapsible anvil assembly and applicator instrument for a surgical stapler apparatus. U.S. Pat. No. 6,503,259 is relevant to the present invention in that it discloses a surgical anastomotic fastener array (10 in the '259 patent) comprising a plurality of fasteners (11 of the '259 patent) each having a tissue piercing element (12 of the '259 patent), wherein the fasteners are aligned in an annular array of a first diameter at least prior to anastomosis and are designed to expand to form an annular array of a second larger diameter and then contract as needed after anastomosis. The '259 patent is addressing the same broad concern of the resulting anastomotic ring, but the earliest filing date of the '259 patent is, however, not earlier than the conception date of the present invention.

The retractable anvil EEA's discussed above do not address the fundamental problem of the constrictive point formed after luminal anastomosis. These prior art devices simply address the problem of post operative tool removal.

It is the object of the present invention to avoid the drawbacks of the prior art by avoiding the minimal constriction formed at luminal anastomotic sites using anastomotic staplers (i.e., EEA's). It is a further object of the present invention to provide anastomotic staplers which are easy to manufacture and utilize. A further object of the present invention is to provide both intraluminal anastomotic end to end staplers and extraluminal anastomotic end to end staplers.

SUMMARY OF THE INVENTION

The above objects are achieved with the anastomotic device according to the present invention. The anastomotic device according to the present invention is a surgical stapler that will form an anastomosis between existing lumen sections in an end to end alignment forming the anastomosis site with a minimal diameter generally equal to or greater than the normal inner diameter of the anastomized lumen sections, with the lumen sections in a normal relaxed condition. The anastomotic device of the present invention will preferably utilize conventional staples formed in a pair of offset annular arrays of staples to couple the end of a first lumen section to the end of a second lumen section.

A first embodiment of the present invention forms the anastomotic device as an intraluminal end to end surgical stapler. The intraluminal surgical stapler fires staples, or other fastening devices, from a stapling head to an adjacent anvil. In accordance with the present invention, both the head and the anvil can be moved from a retracted position having a first relative diameter to an expanded position of a second larger diameter. The expansion of both the head and the anvil allows the anastomotic device to be positioned in the lumen to be attached with minimal interference and then expanded to an enlarged firing position, wherein when fired the anastomotic ring formed by the array of staples is positioned at a diameter preferably at least as large as the minimum diameter of the adjacent lumen sections. After firing, the head and anvil of the stapler of present invention can both be retracted to allow for easy withdrawal of the stapler from the anastomized lumen.

In one embodiment of the present invention, the head will be formed of a plurality of wedge-shaped arc segments which move radially and align in an expanded position to form the annular head. The arc segments may be in the form of inner wedge-shaped segments moved by an actuator and outer segments guided by the inner wedge-shaped segments. The wedge-shaped segments may be moved into the expanded or retracted positions by being coupled to the actuator in the form of axially movable wedges controlled by the user.

Another embodiment of the present invention will form the annular head as a plurality of arc segments that slide together with the segments formed in an overlapped position in the retracted state and rotate into contracted and expanded positions. A further embodiment of the present invention will hinge various arc segments together to allow the segments to pivot between a retracted position of a minimal diameter and an expanded position forming the annular head ready for firing.

Each individual arc segment of the head portion will include staples which combine to form the array of staples in the expanded position. One key aspect of the present invention is that each arc segment has a separate firing mechanism as well as a knife actuating mechanism independently associated with each segment. Each segment will have an arcuate knife portion which will combine and overlap with the knife portions of adjacent segments to form a continuous annular knife arrangement when the head is in the expanded position. In this manner, the knife portions and staples of each individual segment will combine to form the dual stapling array and annular knife well-known to those skilled in the art (except of a larger diameter relative to the body of the stapler). The firing mechanism of each individual segment is additionally coupled to the controller of the stapler in a manner which accommodates movement of the individual segments between the retracted and expanded positions. This construction of the segments allows for the segments to be formed in the hinged arrangements, spirally attached arrangements or wedge arrangements discussed above. Many other possible relatively movable combinations may be constructed with the individual segment construction of the stapler of the present invention.

Another aspect of the present invention is to form an external end to end anastomotic surgical stapler. The external stapler according to the present invention is designed to clamp around lumen sections to be attached. The extraluminal stapler according to the present invention is designed to form an anastomizing ring of sutures external to the connected lumen sections. The external stapler according to the present invention forms a pair of annular arrays of staples around an outwardly extending flange of the connected lumen sections.

In one embodiment according to the present invention, the extraluminal stapler is formed of two opposed stapler units with each stapler unit formed of two halves hinged together. The extraluminal stapler will include a mechanism for pulling the lumen to be attached around the stapling face of each stapling unit. The extraluminal stapler according to the present invention will additionally include a mechanism for aligning the stapling head and anvil portions of the opposed stapling units with each other as well as a firing mechanism for firing the arrays of staples in the stapling units. One embodiment of the present invention will form each stapling unit as an anvil and head portion hinged together which couples with an adjacent hinged anvil and head portion of the opposed stapling unit.

The present invention would be particularly applicable for bowel resections as will be understood by those of ordinary skill in the art, but is not intended to be limited thereto. It can be used in many other applications such as, but not limited to, vascular anastomosis, gastrointestinal anastomosis, esophageal anastomosis and essentially any hollow lumen within the body. Further, the specific embodiments of the invention include a variety of unique features that can be incorporated separately or in various combinations into other stapling and surgical devices for improving those devices.

One advantage of the present invention is a minimally invasive surgical stapler that will assist in stapler placement because the diameter of the stapler (i.e. the largest diameter portion, specifically the head and anvil of the stapler) is smaller during insertion and retraction than at firing.

Another advantage of the present invention is having a closed loop EEA stapler with the trimming knife formed by individual knife segments. This feature of the present invention may be utilized for firing the knife segments individually, or in a given sequence, or simultaneously (as utilized in the illustrated embodiments of the present invention.

Another feature of the present invention is the accommodation of multiple anvil and multiple head controls in a surgical stapler. One present illustrated embodiments provide separate controls for expansion/retraction of the anvil and for axial movement of the anvil. This illustrated embodiment further provides independent control for expansion/retraction of the head and for firing of the knife blade and staples. This system of multiple independent control may be modified to perform a variety of separate control features for the anvil and head portions of an EEA stapler.

Another feature of the present invention is the provision of an EEA stapler with a staple and knife firing mechanism that accommodates relative motion of the head portion containing the staples and the firing mechanism.

Another feature of the present invention is the provision of an alignment mechanism that aligns and locks the anvil and head portion together prior to the firing of the staples or the knife.

Another feature of the present invention is the provision of a closed loop surgical stapler for end to end anastomosis in which the stapler extends around the outside of the lumen portions being anastomised.

These and other advantages of the present invention will be clarified in reviewing the detailed description of the preferred embodiments taken together with the attached figures wherein like reference numerals represent like elements throughout.

BRIEF DESCRIPTION OF THE DRAWINGS

FIG. 5b is a radially inner side view of the head segment illustrated in FIG. 5a;

FIG. 6a is a perspective view of an intraluminal anastomotic surgical stapler utilizing the expandible head illustrated in FIGS. 2a and 2b and the expandible anvil illustrated in FIGS. 3a and 3b;

FIG. 6b is a partial section of a portion of the stapler illustrated in FIG. 6a taken along line VIb—VIb in FIG. 6a;

FIG. 6e is a side view partially in section of a distal end of the stapler illustrated in FIG. 6a;

FIG. 7b is a side view of the complete extraluminal surgical stapler illustrated in FIG. 7a;

FIG. 8b is an end view of the lumen and clips illustrated in FIG. 8a;

DETAILED DESCRIPTION OF THE PREFERRED EMBODIMENTS

Figure 1A:
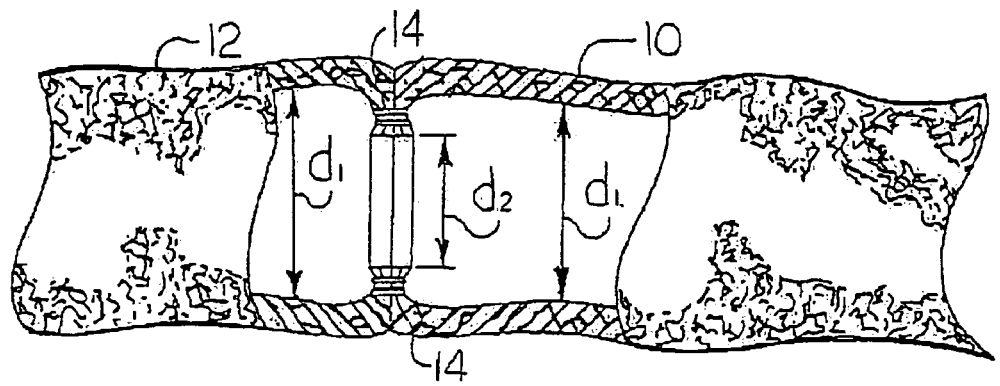
FIG. 1a is a side view, partially in section, of a pair of lumen sections anastomized using existing intraluminal anastomotic staplers.
Figure 1B:
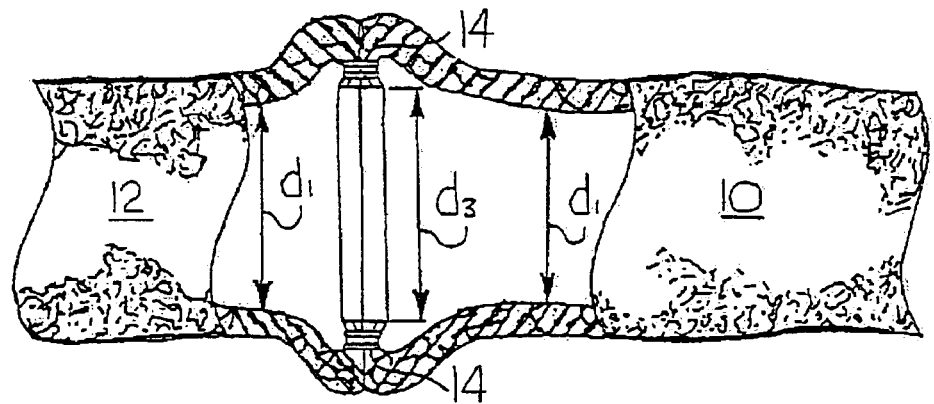
FIG. 1b is a side view, partially in section, of a pair of lumen sections anastomized with an anastomotic stapler according to a first embodiment of the present invention.
Figure 1C:
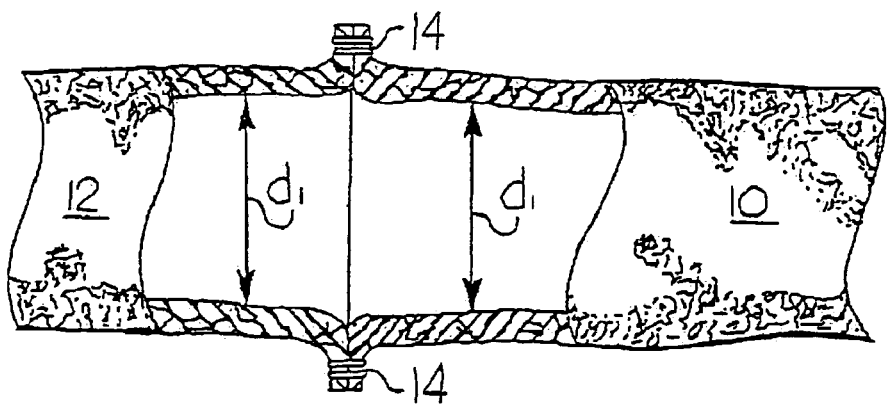
FIG. 1c is a side view, partially in section, of a pair of lumen sections anastomized using an anastomotic stapler according to a second embodiment of the present invention.

The objects and advantages of the present invention can be best clarified in reviewing the surgical results illustrated in FIGS. 1a, 1b and 1c with the prior art surgical staplers (FIG. 1a) and various embodiments of surgical staplers (FIGS. 1b and 1c) of the present invention, respectively. FIG. 1a illustrates lumen sections 10 and 12 anastomized with a conventional intraluminal anastomotic stapler (i.e. an EEA). The first lumen section 10 and second lumen section 12 will have a nominal diameter $d_1$. With existing end to end anastomotic staplers, the anastomosis site, sometimes referred to as an anastomosis ring, formed by an array of staples 14 will have a smaller diameter $d_2$ than the nominal luminal diameter $d_1$. In addition to the constrictive point formed by the smaller diameter $d_2$, with the existence of (1) the array of staples 14, (2) the additional tissue formed by the coupled lumen sections at the anastomosis site, and (3) the scar tissue forming around the anastomotic ring, this constricture or constriction will have greater rigidity, i.e., less flexibility, than the associated lumen tissue. As discussed above, the object of the present invention is to avoid this constrictive point and the possible detrimental effects associated therewith. Of course, the detrimental effects associated with a more rigid constricture in an anastomized lumen would depend on the particular lumen which is coupled together. However, whether connecting together a bowel in vascular anastomosis, or connecting any lumen within the body such constrictures are universally undesirable.

FIG. 1b illustrates the anastomosis of lumen sections 10 and 12 with a surgical stapler 100 according to a first embodiment of the present invention. The anastomotic stapler 100 of the invention associated with the results shown in FIG. 1*b* is described in detail in FIGS. 2*a* and 2*b*, 3*a* and 3*b*, 4*a* and 4*b*, 5*a*–*g*, and 6*a*–6*e*. As illustrated in FIG. 1*b*, the anastomotic ring or suture site formed by the array of staples 14 has an inner diameter d.sub.3, which is relatively larger than the diameter d.sub.2 associated with conventional staplers. The diameter d.sub.3 is preferable formed at least as great as diameter d.sub.1 of the adjacent lumen sections. In this manner, the detrimental effects of the constricture site can be minimized. It should be appreciated that the inner area of the anastomized lumen is associated with the square of the diameter such that minimal improvements in the diameter of d.sub.3 over d.sub.2 of the prior art will result in substantial increases in the area of the lumen. It is preferred that in the present invention, the diameter d.sub.3 at the anastomotic ring be at least as great, or greater than the nominal diameter d.sub.1 of the associated lumens to avoid any problems with constricture. The relative increase or expansion of the anastomotic ring possible with the device according to the present invention will be associated with the tissue flexibility of the lumen sections for which the particular stapler is designed. For example, tissue forming a bowel (relatively flexible) and tissue forming vascular lumens (less flexible compared to the bowel) would accommodate different relative dimensions for d.sub.3 compared to d.sub.1 at the anastomotic site. However, the general operative concepts of an intraluminal bowel stapler according to the present invention is the same as an intraluminal vascular stapler according to the present invention.

FIG. 1*c* illustrates an end to end anastomosis of two lumens 10 and 12 with an array of staples 14 utilizing an extraluminal surgical stapler according to a second embodiment of the present invention. The stapler according to the second embodiment of the present invention forms an outer anastomotic ring with the array of staples having a diameter greater than d.sub.1, the normal diameter of the lumen, such that the anastomosis site forms no constricture. The relative positioning of the array of staples 14 will again depend on the particular lumen being anastomized. Examples of the stapler forming this anastomosis are illustrated in FIGS. 7*a*, 7*b*, and 8*a*–8*e* below.

Figure 2A:
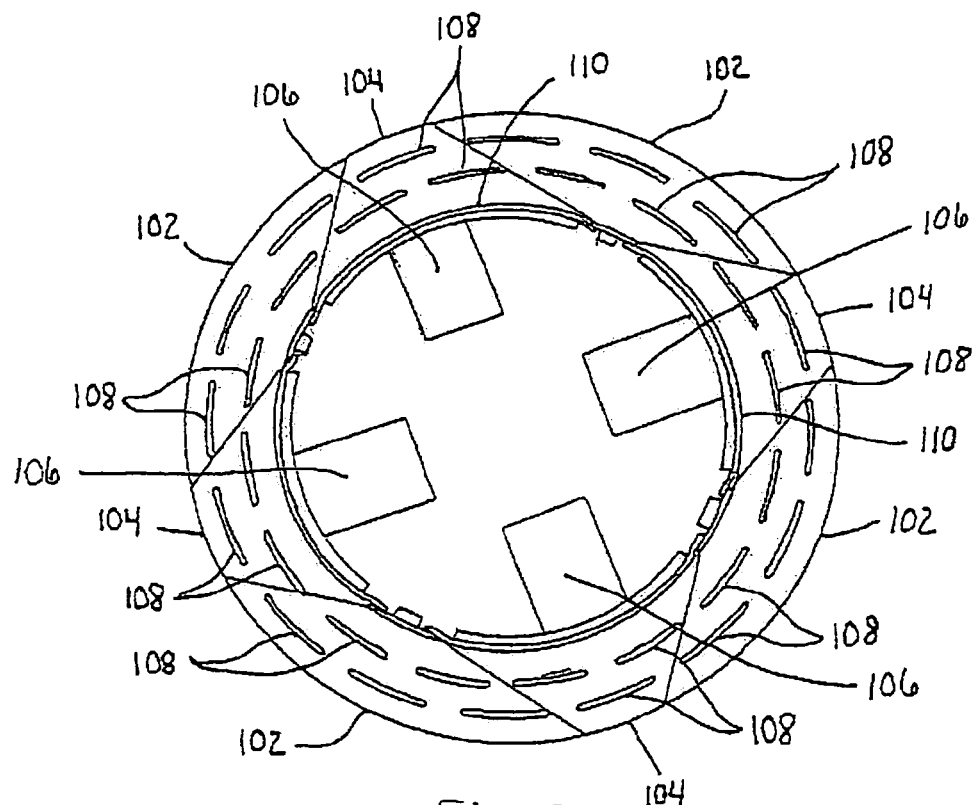
FIG. 2a is a schematic plan view of an intraluminal end to end anastomotic stapling head according to the first embodiment of the present invention with the head in the expanded, firing position.
Figure 2B:
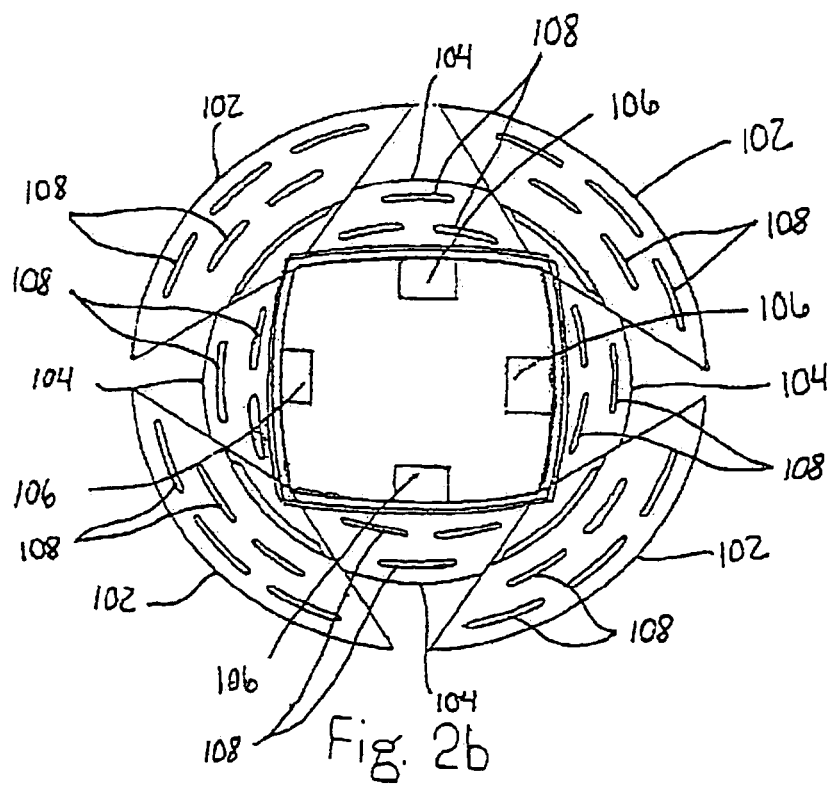
FIG. 2b schematically illustrates the head illustrated in FIG. 2a in the retracted position.

FIGS. 2*a* and 2*b* schematically illustrate an expandable head 90 for the intraluminal anastomotic stapler 100 according a first embodiment of the present invention. The expandable head 90 is formed of a plurality of arc segments which interconnect in an outer firing position to form the annular expanded head 90 as shown in FIG. 2*a*. The individual segments shown in the embodiment illustrated in FIGS. 2*a* and 2*b* comprise outer wedge-shaped segments 102 and inner wedge-shaped segments 104. The inner segments 104 are moved radially inwardly and outwardly by individually associated wedge elements 106. The side wedge-shaped engaging surfaces of the inner segments 104 will force the outer segments 102 into the expanded condition. The inner segments 104 can be pinned to the outer segments 102 in a manner to be described later such that retraction of the inner segments 104 to the retracted position shown in FIG. 2*b* will also pull the outer segments 102 toward the retracted position.

The structure of the individual segments 102, 104 is discussed later in greater detail. Generally speaking, each segment 102, 104 includes a plurality of staple receiving slots 108 in a staggered annular array consisting of both an outer ring and an inner ring of staples receiving slots 108. As clearly evident in the figures, it is an important aspect of the present invention that the division between adjacent segments 102, 104 needs to be accomplished between the staple receiving slots 108. As can be seen in the figures, in the expanded position, the segments 102, 104 combine to form a standard annular array of staples 14 in an offsetting overlapping arrangement. Additionally, each segment 102, 104 includes, at a radial inner side thereof, with knife portions 110 which combine in the expanded position to form an annular knife which provides a trimmed inner edge to the anastomized lumen as is conventional. In order to ensure a complete annular knife in the firing position, and therefore a complete annular smooth cut to the lumen, knife portions 110 of the inner segments 104 overlap with the knife portions of the adjacent outer segments 102 as generally illustrated in the figures. As can be seen in FIGS. 2*a* and 2*b*, the wedge-shaped interacting arc segments 102, 104 of the head 90 will allow it to be moved between retracted and expanded positions. It should be evident that the present invention is not intended to be limited to the specific number of segments illustrated in FIGS. 2*a* and 2*b*. A minimization of the diameter in the retracted position can be obtained with as little as three inner wedge-shaped segments 104 spaced about the periphery of the head 90. The number, positioning and specific shape of the segments 102, 104 can be changed as desired in order to allow for the desired degree of expansion. Other factors affecting the number and shape of the individual segments 102, 104 will be the number and length of the specific staples 14 utilized in the inner and outer rings. All of these factors can be considered in designing a specific expanding head 90 which expands to the degree desired.

Figure 3A:
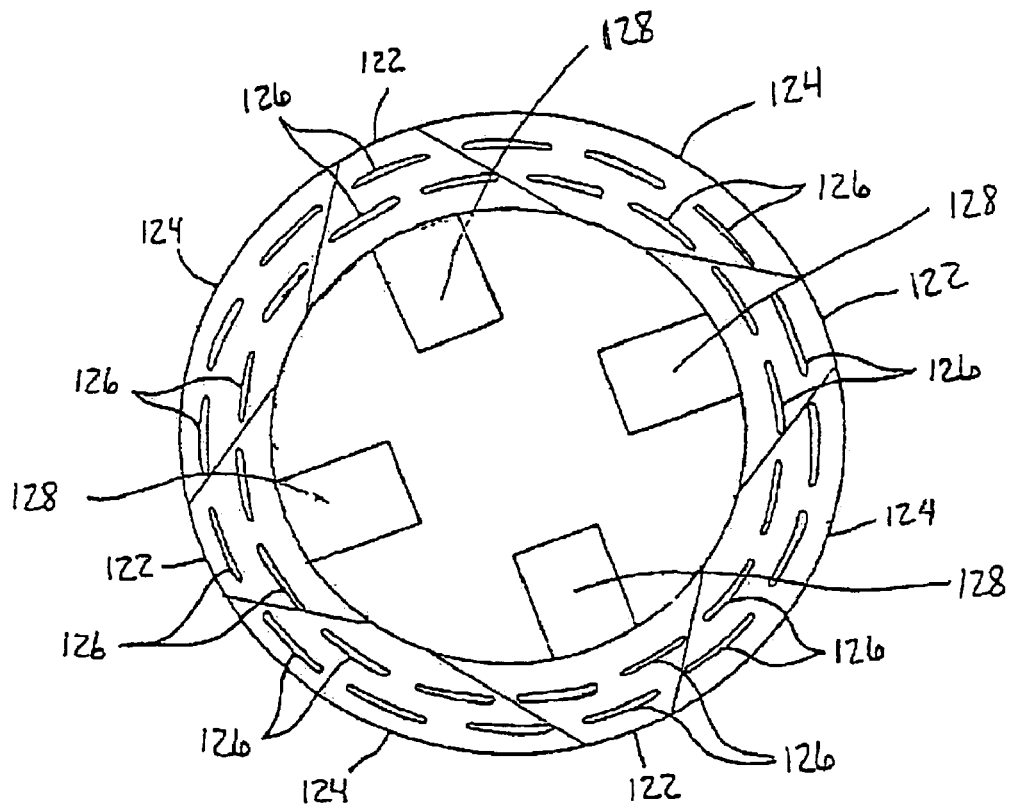
FIG. 3a schematically illustrates an expandable anvil associated with the anastomotic stapler having the expandable head illustrated in FIGS. 2a and 2b.
Figure 3B:
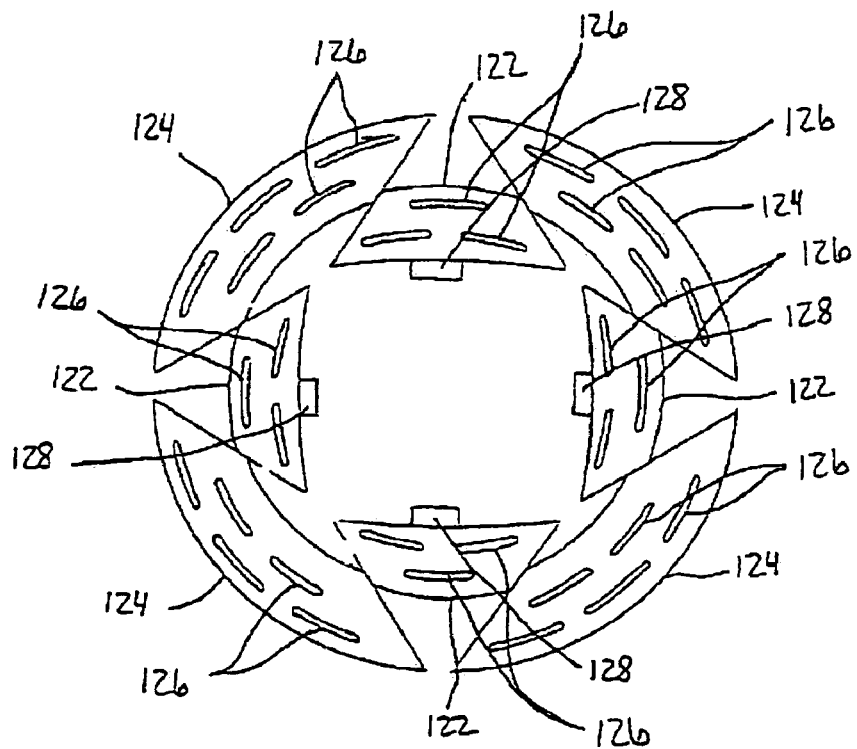
FIG. 3b schematically illustrates the anvil portion of FIG. 3a in a retracted position.

FIGS. 3*a* and 3*b* illustrate the expanding anvil 120 utilized with the stapler 100 according to the present invention. These figures illustrate that the anvil 120 is formed of inner segments 122 and outer segments 124 similar to the inner segments 104 and outer segments 102 of the head 90. The anvil 120 in the expanded position forms an annular ring with conventional staple engaging grooves 126 which will correspond to the staple receiving slots 108 of the head 90 for cinching the fired staples 14 as known in the art. The inner and outer segments 122, 124 can be pinned together and the inner segments 122 can be moved by a wedge 128 similar to the mechanism for the head 90. The anvil 120 construction is significantly simpler than the head 90 construction for a variety of reasons. First, the anvil 120 construction is not limited to forming the staple engaging grooves 126 entirely on one segment 122 or 124. These expanding anvil segments 122, 124 can be formed essentially in any position even dividing a staple receiving groove 126. This provides significantly greater flexibility in deciding where to put the inner and outer segments 122, 124. An additional aspect to making the anvil 120 significantly easier to design and operate is that there is no knife or staple firing mechanisms which needs to be incorporated into the expanding and retracting anvil 120. In fact, the prior art illustrates that expanding anvils have been well-known in the art, and many of these constructions can also be incorporated into the design of the present invention. For the sake of simplicity, however, the design of the anvil 120 is essentially the same as the design of the expanding head 90 illustrated in FIGS. 2a and 2b.

Figure 4A:
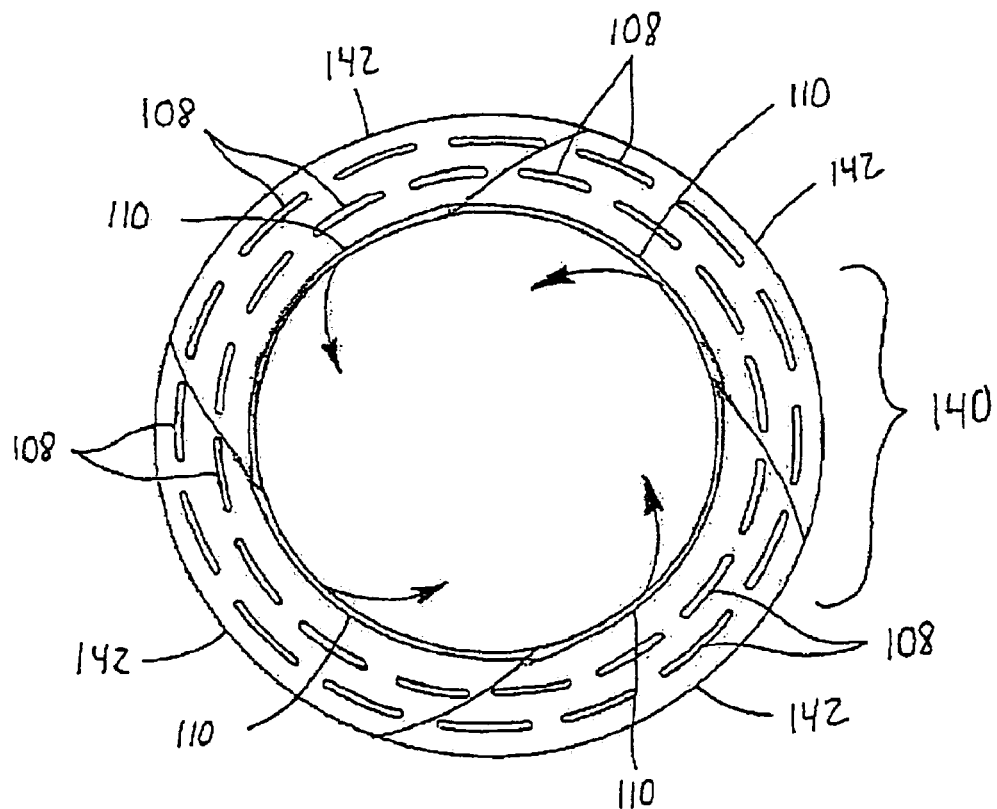
FIG. 4a schematically illustrates a spirally retracted and expandable head for an intraluminal end to end surgical stapler according to a second embodiment of the present invention.
Figure 4B:
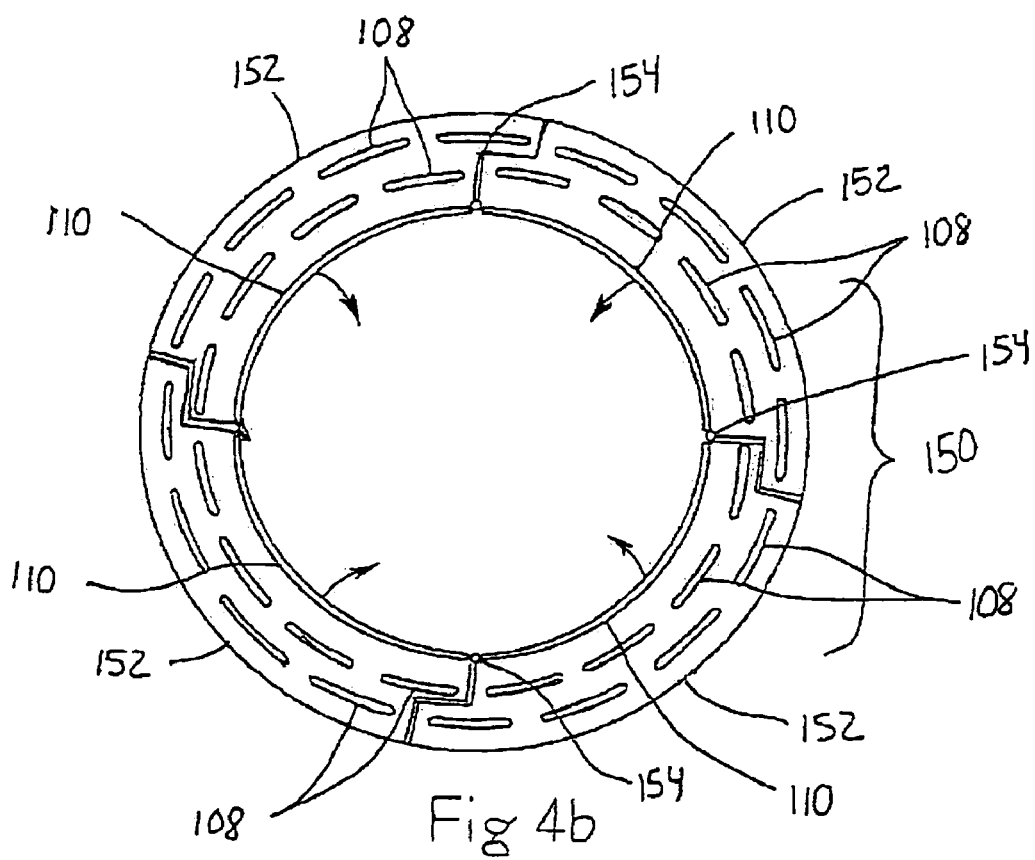
FIG. 4b schematically illustrates a hinged expandable and retractable head for an intraluminal end to end surgical stapler according to a third embodiment of the present invention.

FIGS. 4a and 4b are intended to illustrate alternative expanding head mechanisms according to the present invention. FIG. 4a illustrates an expanding head 140 according to one embodiment of the present invention in which the head 140 is formed of individual segments 142 which can slide past each other in an overlapping arrangement to contract in a spiral fashion as illustrated by the arrows. In place of an actuating wedge, the actuating mechanism may be a rotating cam type operator, although a variety of segment 142 moving mechanisms can be envisioned.

FIG. 4b illustrates yet another embodiment for an expanding head 150 for a stapler 100 of the present invention in which individual segments 152 of the head 150 are hinged together by hinges 154 to move between expanded and contracted positions. This embodiment illustrates three hinges 154 and one open connection which can have these segments 152 snap together to form the continuous ring. The number of individual segments 152 may be selected as desired. The hinges 154 may include spring-biasing to help move the segment 152 to either the expanded or retracted positions. A mechanical actuator linearly moving along the length of the stapler 100 would be used to move the segments 152.

FIGS. 5a–5g illustrate the details of the individual arc segments 102, 104 forming the expandable head 90 illustrated in FIGS. 2a and 2b. The segments 102, 104 are discussed in detail and illustrated associated with the specific expanding head 90 illustrated in FIGS. 2a and 2b. However, the general concepts of these individual segments 102, 104 can be easily extrapolated for many different embodiments, such as those illustrated in FIGS. 4a and 4b. The key features of the arc segments 102, 104 for the expanding head 90 according to the present invention is that the individual segments 102, 104 have independent firing mechanisms for the staples 14 and the knife portions 110 that are associated with that segment 102, 104. Additionally, the firing mechanism accommodates the relative motion of the segments 102, 104 between the retracted and expanded positions. As will be evident in the description of FIGS. 5a–5g, these components utilized in the segments 102, 104 of the present invention can be utilized in the expanding heads 140 and 150 illustrated in FIGS. 4a and 4b as well as a wide variety of other configurations for an expanding head having separate segments the user may contemplate.

Figure 5A:
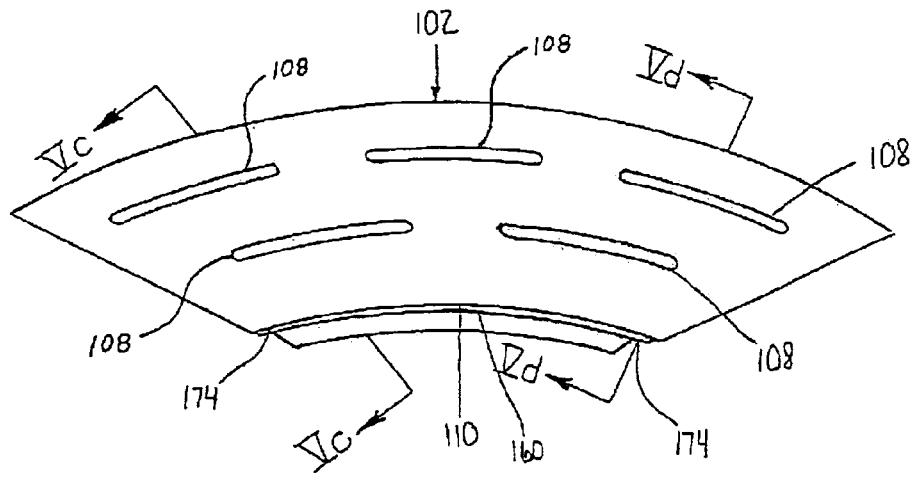
FIG. 5a is a plan view of an individual outer head segment of the head illustrated in FIGS. 2a and 2b.
Figure 5B:
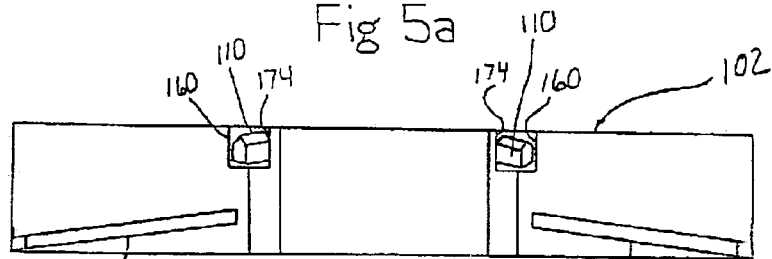
Figures 5C, 5D:
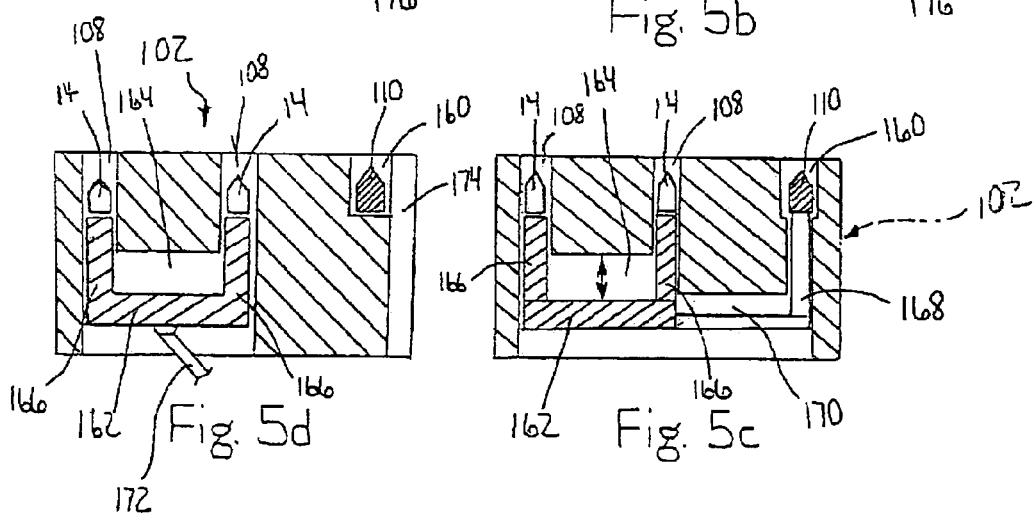
FIG. 5c is a sectional view of the head segment illustrated in FIG. 5a taken along line Vc—Vc.
FIG. 5d is a sectional view of the head segment illustrated in FIG. 5a taken along line Vd—Vd.

FIG. 5a illustrates a plan view of the outer segment 102 of the expanding head 90 illustrated in FIG. 2a. The outer segment 102 includes a plurality of slots 108 for receiving staples 14 therein as shown in FIGS. 5c and 5d. On the radial inner side of the segment 102 is a groove 160 extending across the entire segment 102. The arcuate knife portion 110 is positioned in the groove 160. The knife portion 110 and staples 14 are all fired through a common firing mechanism which can be best seen in FIGS. 5c and 5d. Essentially, a base plate 162 is positioned in a recess 164 extending along the length of the segment 102. The base plate 162 includes a plurality of pusher bars 166 extending into the individual staple receiving slots 108 for supporting and firing the staples 14. As illustrated in FIG. 5c, the base plate 162 is positioned in the recess 164 with enough room for movement (longitudinally of the stapler 100) for allowing the firing of the staples 14 and the knife portion 110. Additionally, the knife portion 110 is attached to the base plate 162 through a series of L-shaped arms 168 at spaced locations along the base plate 162. The L-shaped arms 168 extend through slots 170 in the segment 102. The base plate 162 is secured to an actuation rod 172 at the bottom thereof for moving the base plate 162 in the segment 102 for firing of the staples 14 and actuation of the individual knife portion 110.

As discussed previously, the individual knife portions of the various segments 102, 104 will overlap to assure that a complete annular circle is formed and cut by the combined knife portions 110. In order to easily accommodate the overlapping of the outer edges of the segments 102 near the groove 160 are cut out at recess 174 to allow the overlapping portions of the knife portions 110 of the inner segments 104 discussed below to easily overlap the knife portions 110 of the outer segments 102 when the inner segments 104 are pushed into position. Additionally, the outer segments 102 are provided with pin receiving grooves 176 for pinning the outer segments 102 to the inner segments 104. The grooves 176 will allow the inner segments 104 to follow a defined path of movement during the expansion and contraction as well as pull the outer segments 102 towards the retracted position when the inner segment pin 178 reaches the radially inner extent of the groove 176 during the retraction of the expandable head 90.

In view of the complex shape, it is expected that the segments 102, 104 may most easily be formed of an injection molded plastic design, however, any construction technique and material is contemplated.

Figure 5E:
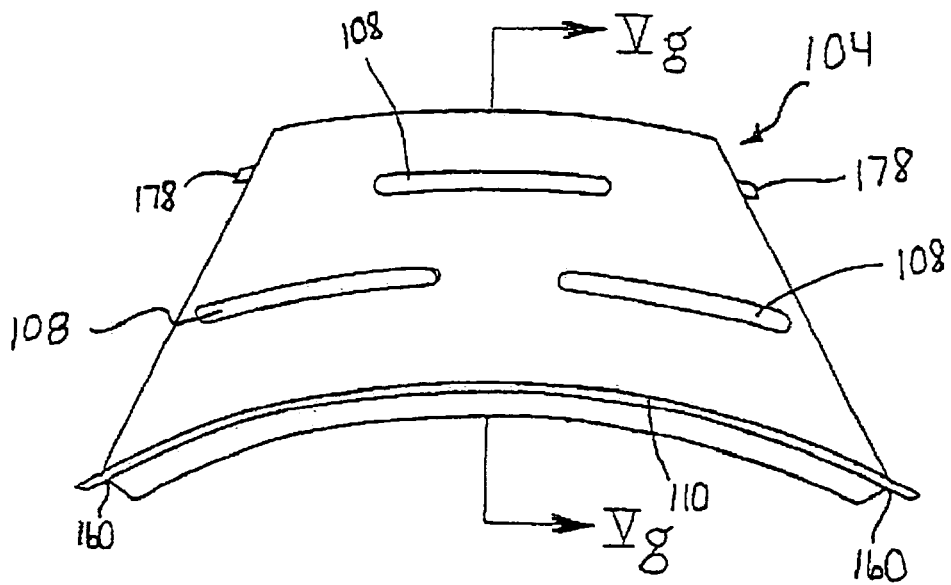
FIG. 5e is a top plan view of an inner head segment illustrated in FIGS. 2a and 2b.
Figure 5F:
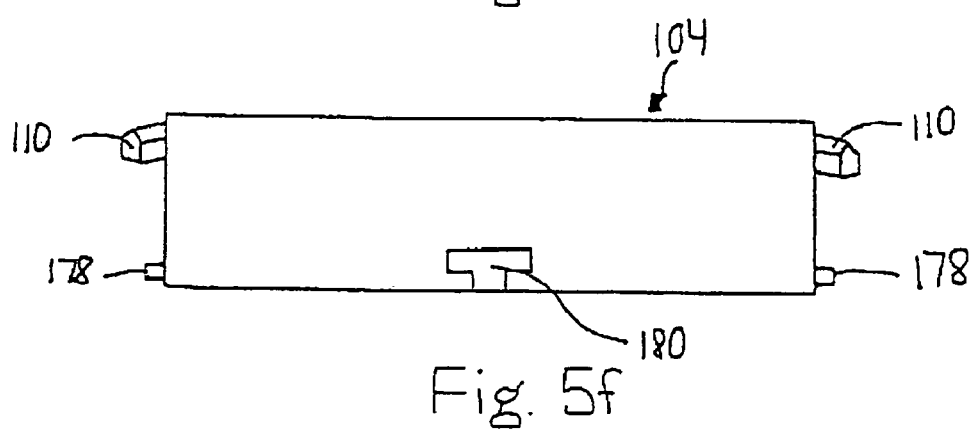
FIG. 5f is a radially inner side view of the inner head segment illustrated in FIG. 5e.

FIG. 5e illustrates a plan view of the inner segments 104 for the expandable head 90 in FIGS. 2a and 2b. The inner segment 104 additionally includes staple receiving slots 108 in two annular arrays similar to the staple receiving slots 108 formed in the outer segment 102. Furthermore, the inner segment 104 includes a groove 160 on the radially inner edge thereof receiving an annular knife portion. As illustrated in FIGS. 5e and 5f, the annular knife portion 110 of the inner segment 104 extends beyond the edges of the segment 104 to provide on overlapping blade section which would be received in the recess 174 of the outer segments 102 shown in FIG. 5a. As discussed above, this construction ensures the overlapping of the knife portions 110 to form a complete annular knife blade ring 178. The inner segments 102 will additionally include the pins on the sides thereof for engaging with grooves 160 formed on the sides of the outer segment 102 thereby keying the segments 102, 104 together.

Figure 5G:
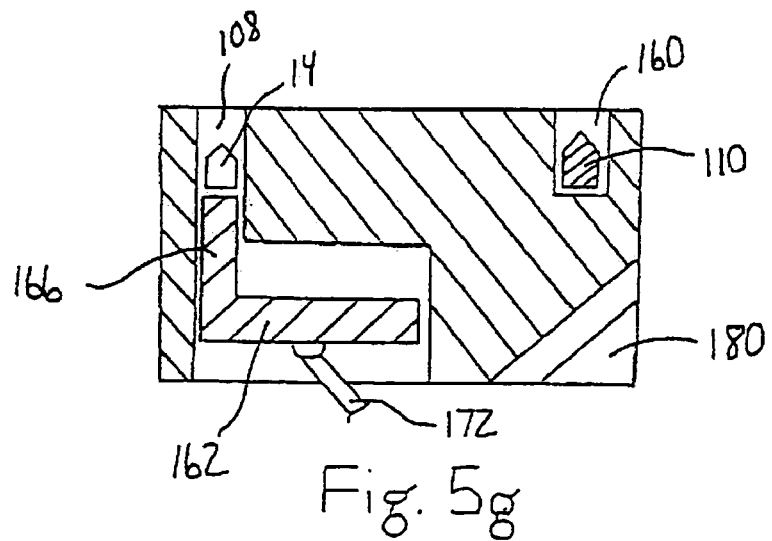
FIG. 5g is a sectional view of the inner head segment shown in FIG. 5e taken along line Vg—Vg.

As shown in FIG. 5g, the inner segment 104 will additionally include a firing mechanism comprised of a base plate 162 with staple projections extending vertically upward into the staple receiving slots 108. The base plate 162 will also be coupled to the knife portion 110 at spaced locations by L-shaped arms (not shown) extending through slots (not shown) in the same manner as in the outer segments 102 disclosed above in FIGS. 5a and 5c.

The inner segments 104 additionally include a beveled T-shaped slot 180 receiving a wedge rod 182 and wedge element 106 therein which operates to move the inner segments 104 and the outer segments 102 for expanding and contracting the head 90. The T-shaped slot 180 is intended to be just one configuration for tying the movement of the segments 102, 104, both in the expansion and retraction mode, to the movement of the controlling wedge rod 182 and attached wedge element 106. Other mechanical connections and actuation mechanisms are contemplated within the scope of the present invention. However, it is believed that the simple mechanical coupling of the components as illustrated is generally preferable to a spring-biasing operation which may not be successful if the forces of the operating spring do not overcome friction or other forces in the stapling environment. Consequently, it is believed that the operating mechanism of the present invention provides a mechanically simple and highly reliable method for actuating and moving the expandable head 90.

It will be appreciated that the specific construction of the inner and outer segments 102, 104 are not limited to the shapes illustrated. The general construction can be expanded to any segment shape such as those illustrated in FIGS. 4a, 4b or many other shapes that can be contemplated for forming an expandable head 90 for a stapler 100.

FIGS. 6a–6e illustrate the details of an intraluminal anastomotic stapler 100 with an expanding head 90 illustrated in FIGS. 2a and 2b as well as an expanding anvil 120 illustrated in FIGS. 3a and 3b. The stapler 100 looks essentially like a conventional EEA stapler having an elongated body 190 of generally circular cross-section further including the expanding head 90 and anvil 120 at a distal end thereof. The expanding anvil 120 will have a length slightly longer than an anvil of a conventional EEA to accommodate the expanding anvil mechanism. At the opposite end of the body 190, the stapler 100 will have generally conventionally shaped controls 192, 194 for advancing and retracting the anvil 120 relative to the head 90 and for firing of the staples 14. Specifically, a rotatable controller 192 is utilized for expanding and contracting the anvil 120 and clamping the lumen sections 10 and 12 together and a pair of pivoted firing grips 194 are utilized for firing the staples 14. Additionally, the stapler 100 may include a known safety release (not shown) which does not allow the staples 14 to be fired unless the anvil 120 is in an acceptable proximity of the head 90. This safety mechanism may also be tied to the expanding mechanism, to be described, such that the firing of the staples 14 would not be possible unless the head 90 and anvil 120 are also expanded to the appropriate expanded, firing positions.

With regard to the expansion control, a pair of finger grip controllers 196 extend from opposite sides of the housing or body 190 extending from a Z-shaped slot 198. When desired to expand, the user can grip one or both expansion controllers 196, pivot them slightly out of the retracted position (i.e., one leg of the z-shaped slot 198) moving axially along the length of the housing in a axial portion of the Z-shaped slot 198 and then when fully expanded move the controllers 196 into the upper leg of the Z-shaped slot 198 to hold the anvil 120 and head 90 in the fully expanded position. After firing, the process can be reversed for retracting both the anvil 120 and head 90. It will be appreciated that within this construction, the outer diameter of the body 190 can be formed approximately equal with the diameter $d_1$ of the lumen sections 10 and 12 to be anastomized. It will be understood that the expanded head 90 and anvil 120 will expand the lumen sections to a stretched condition such that the anastomized ring will be formed at a diameter $d_3$, preferably at least as great as the normal unstretched diameter $d_1$ of the lumen sections 10 and 12 to be anastomized.

Figure 6B:
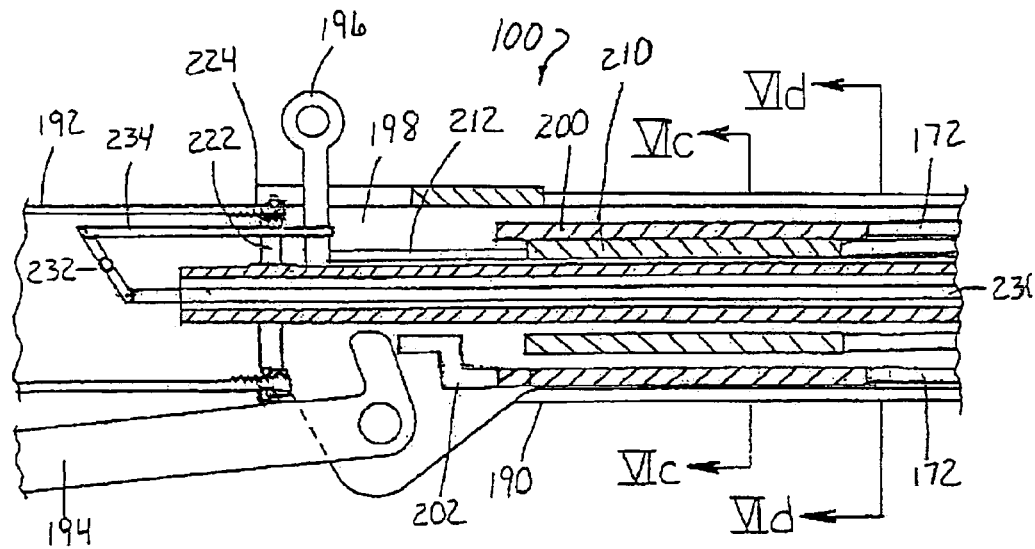

FIG. 6b is a sectional view of the controlling portion taken along two radial sections offset 90 degrees to best illustrate the expansion, clamping and firing controls (196, 192, 194) of the present invention.

Figure 6E:
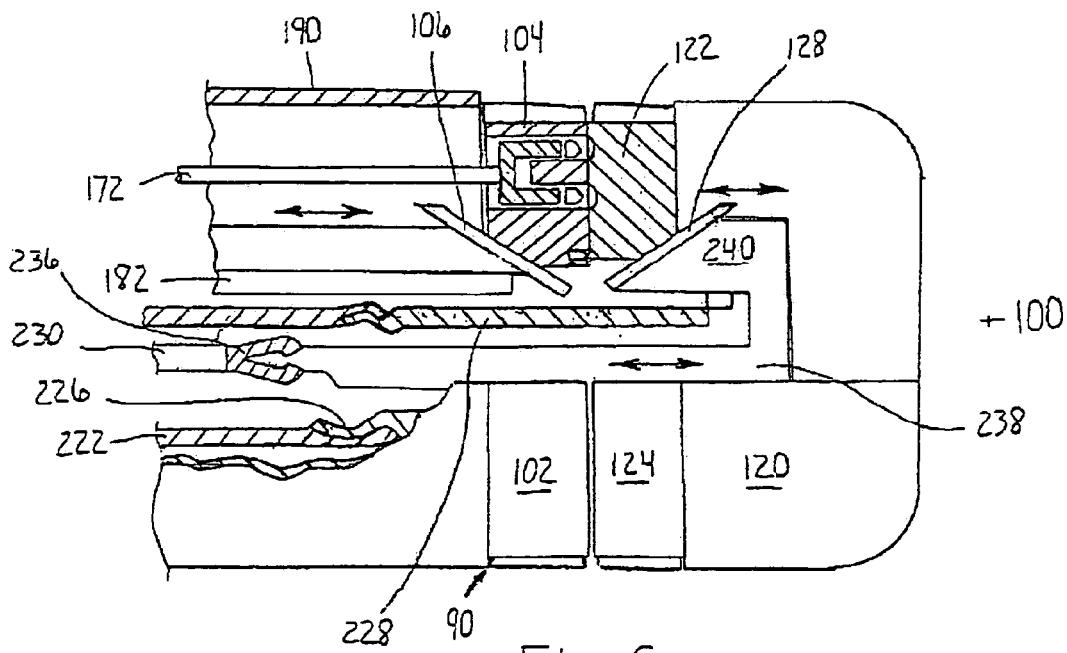
Figure 6C:
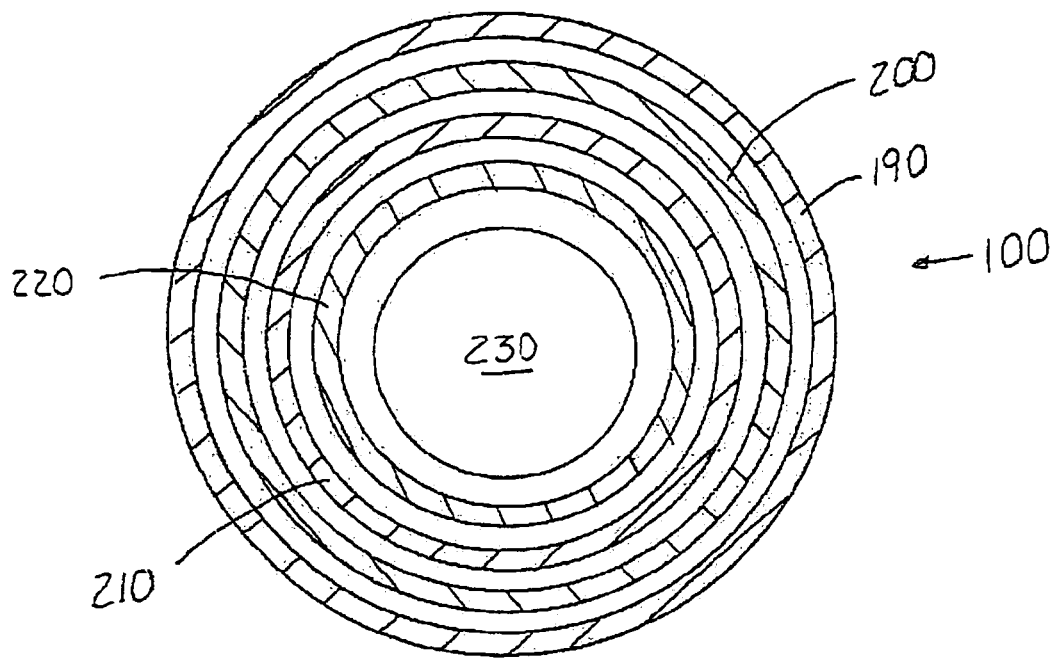
FIG. 6c is a cross-sectional view of the stapler illustrated in FIG. 6b taken along line VIc—VIc.

As shown in FIGS. 6b and 6c, for at least a portion of the housing or body 190, the operating mechanisms are formed of a series of concentric independently operated sleeves for controlling the various functions of the stapler 100 of the present invention. It should be understood that the sleeves are intended for limited axial motion along the length of the body 190 and may be formed of either a rigid or slightly flexible material. In other words, the body 190 may have a certain curvature along its length, as is known in the art, and the operating mechanism can be made of a material to accommodate such curvature.

Beginning next to the annular housing or body 190 is a firing ring 200 which is utilized for actuating the firing mechanisms in the individual head segments 102, 104. At one end of the axially movable firing ring 200, a series of the firing or actuation rods 172 are attached which extend from the firing ring 200 to each individual base plate 162 of each individual segment 102, 104. The firing rods 172 can be pivotally attached to the firing ring 200 and segments 102, 104 or the rods 172 can be formed sufficiently flexible to accommodate the outward movement of the associated segments 102, 104. The opposite end of the firing ring 200 includes a pair of L-shaped legs 202, only one of which is shown in FIG. 6b, attached to the individual firing grips 194. As can be easily understood by viewing FIG. 6b, when the firing grips 194 are pulled, the legs 202 in the firing ring 200 will be moved axially along the body 190 moving the rods 172, axially along the body thereby pushing the associated base plates 162, firing the individual staples 14 and actuating the individual knife portions 110. It should be appreciated by those of ordinary skill in the art that a wide variety of changes to the firing mechanism can be envisioned. For example, a pull trigger could easily replace the firing grips 194. The firing grips 194 are illustrated since this represents a known acceptable operating mechanism. As discussed above, a safety latch mechanism can be incorporated, if desired, to avoid premature firing of the staples 14. The construction of such safety devices is certainly known to those of ordinary skill in the art.

Figure 6D:
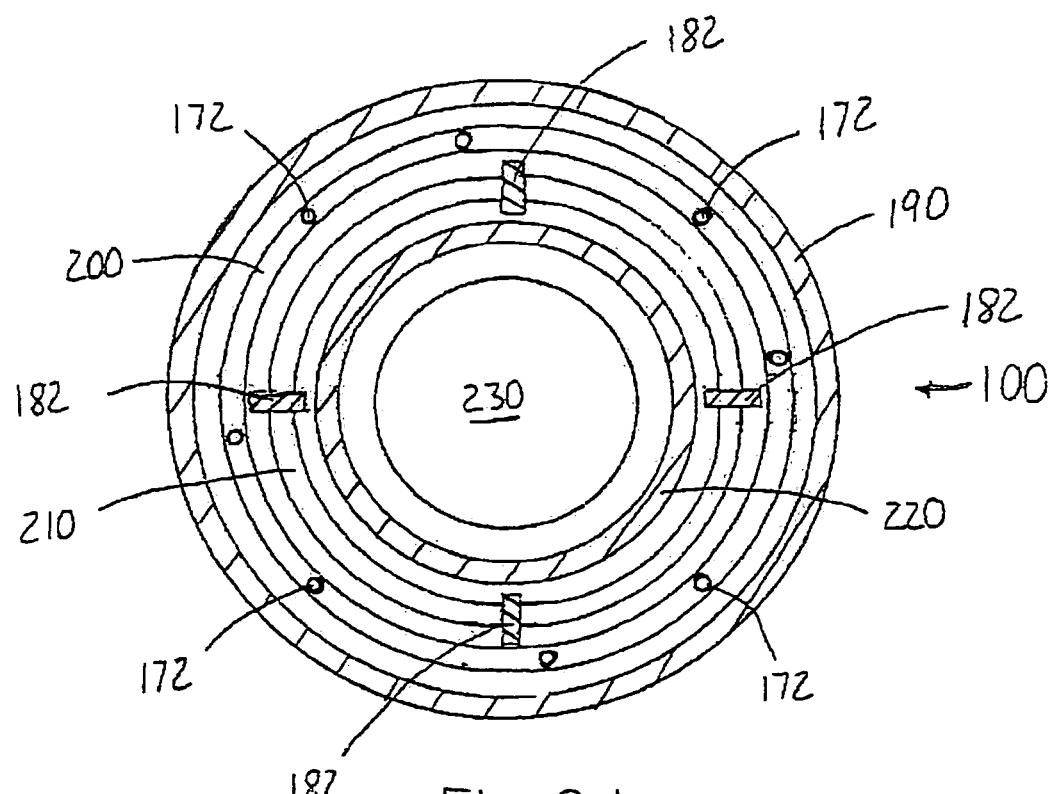
FIG. 6d is a cross-sectional view of the stapler illustrated in FIG. 6b taken along line VId—VId.

Radially adjacent the firing ring 200 is an independently movable wedge ring 210 for moving the head segments 102, 104 as will be discussed. At a forward end of the wedge ring 210 are a series of the longitudinally extending wedge rods 182. The wedge rods 182 and wedge elements 206 combined have a beveled T-shape which is engaged in the T-shaped slot 180 of the inner segments 104 for radially moving the segments 102, 104 as the associated wedge rod 182 and wedge element 106 are moved longitudinally back and forth along the body 190. As illustrated in FIG. 6d, there is one wedge element 106 associated with each inner segment 104. On the opposite end of the wedge ring 210 the wedge ring 210 is secured to the pair of opposite extending controllers 196, only one of which is shown in FIG. 6*b*, by an arm 212 or a linkage, again only one of which is shown in FIG. 6*b*. As can be most apparent in FIG. 6*b*, longitudinal movement of the controller 196 will move the connecting linkage arm 212, the wedge ring 210 and the associated wedge rod 182 and wedge element 106 for radially moving the head segments 102, 104 between the fully extended position shown in FIG. 2*a* and the fully retracted position illustrated in FIG. 2*b*.

Radially adjacent the wedge ring 210 is an anvil stem rod 220 moving linearly in the body 190 for moving the anvil 120 into and out of a clamping position relative to the head 90. At one end of the anvil stem rod 220 is a generally disc-shaped actuator 222 threadedly engaging inner threads 224 on the rotatable controller 192. The rotatable controller 192 is attached to the housing in a manner that allows for rotation such that rotation of the controller 192 will axially move the actuator 222 and the anvil stem rod 220 for moving the anvil 120 essentially in a conventional fashion. As shown in FIG. 6*e*, a distal end of the anvil stem rod 220 has a snap fit connection 226 with an annular anvil connector 228 allowing the anvil 120 to be released from the body as known in the art.

Finally, returning to FIG. 6*b*, the innermost control mechanism is an anvil expanding rod 230 axially movable in the body 90 and adapted for expanding the anvil segments 102, 104 between the retracted and expanded positions. The control end of the anvil rod 230 is connected to the expanding controller 196 through a pivoting linkage 232 and a connecting arm 234. This mechanism allows the axial movement of the controller 196 to be associated with an opposite movement of the expanding anvil rod 230. A distal end of the expanding anvil rod 230 includes a connector 236 having a bayonet type connection with an anvil wedge rod 238 as shown in FIG. 6*e*. The anvil wedge rod 238 is associated with four wedge rod elements 240 which support the wedges 128 received in grooves in the inner anvil expanding segments 122 as shown in FIG. 6*e*. It will be appreciated that in the illustrated embodiment the expanding anvil rod 230 and the anvil wedge rod 238 will only be in a secure fitting relationship when the anvil 120 is appropriately clamped against the head 90. With this construction, it may be helpful to have the anvil wedge rod 238 and the associated segments 102, 104 be spring-biased to the retracted position so that there is a retracting biasing force when the expanding anvil rod 230 is not engaged with the anvil wedge rod 238.

Figure 10:
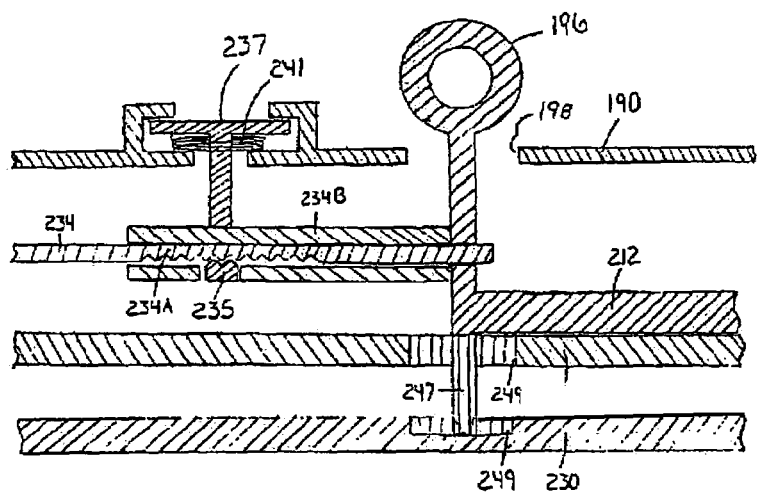
FIG. 10 is a sectional schematic view of a motion accommodation mechanism for the anvil expansion mechanism of a stapler according to the present invention.
Figure 11:
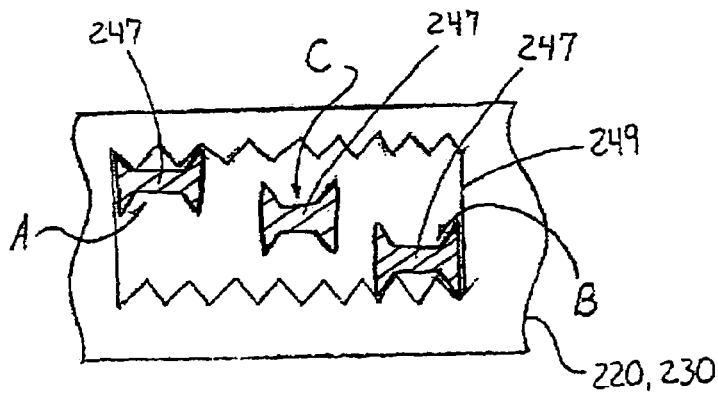
FIG. 11 is a schematic plan view of a lock and release transmission for an anvil stem and an anvil expansion rod of a stapler according to the present invention.

It should be appreciated that other constructions are certainly anticipated, such as having the wedge rod 238 and the expanding anvil rod 230 always coupled when the anvil stem rod 220 and annular anvil connector 228 are connected. In this modification, the anvil expanding rod 230 and the anvil stem rod 220 will need to be moved together. The anvil stem rod 220 is moved relative to the body 190 by rotation of the controller 192. In this modification, the movement of the anvil stem rod 220 can be accommodated by moving the pivoting linkage 232 and the expanding anvil rod 230 with the anvil stem rod 220 and having a lost motion or motion accommodating mechanism be added to the connecting arm 234 to accommodate the change in relative position. One simple example of such a mechanism is illustrated in FIGS. 10 and 11 and essentially includes forming the connecting arm 234 as a telescoping rod having first and second portions 234A and 234B, respectively. The first and second portions 234A and 234B are releasably pinned together with a spring-biased release pin 235 being released by a button 237 (upon which the spring 241 acts) on the body 190 when the controller 192 is desired to be rotated. With such a spring-biased release button 237 and pin 235, the pin 235 is automatically reinserted to connect the first and second telescoping portions 234A and 234B of the arm 234 such that the connecting arm 234 would accommodate the changed length. This embodiment additionally illustrates the use of a releasable lock or transmission between the expanding anvil rod 230 and the anvil stem rod 220. The releasable transmission or lock is in the form of a mating pin 247 extending from the lower end of the controller 196. The mating pin 247 extends into generally identically shaped slots 249 formed in both the expanding anvil rod 230 and the anvil stem rod 220. As shown in FIG. 11 the edges of the slot 249 include mating surfaces that will engage and mechanically lock with the mating pin 247. The slots are designed such that the locking or mating will occur when the controller 196 is in the far left or right radial positions in the z-shaped slot (e.g. when the controller 196 is in the top or bottom leg portions of the z shaped slot) as shown in positions A and B in FIG. 11. When the controller 196 is in the center of the Z-shaped slot for longitudinal movement the pin 247 will be disengaged from the edges of the slot 249 as shown in position C allowing for the relative movement between the expanding anvil rod 230 and the anvil stem rod 220. It will be understood that this transmission will require modification of the Z-shaped slot to accommodate movement of the controller due to axial movement of the anvil, such as increasing the width of the bottom leg of the z in the z shaped slot. This will additionally provide a visual indicator of the relative axial position of the stem prior to expansion of the anvil. This embodiment could utilize the motion accommodating mechanism without the mechanical lock or transmission or the mechanical lock may be used in other EEA staplers as merely a stem position indicating mechanism. This embodiment is described to show the possibility of such a construction.

It should be appreciated that the intraluminal end to end anastomotic surgical stapler 100 illustrated in FIG. 6*a* is utilized in essentially the same manner as existing anastomotic devices with the addition of an expansion and retraction step. Specifically, the stapler 100 is inserted into one lumen section 10 or 12 to be anastomized with the anvil 120 and head 90 either spaced apart or separated as desired by the user. Purse strings attached to the lumen sections 10 and 12 can secure the segments 10 and 12 around the anvil stem rod 220 and/or the anvil connector 228. The controller 196 is rotated to move the anvil 120 and head 90 into at least an initial clamped position. At this point, the anvil 120 and head 90 can be expanded to their extended positions and the staples 14 fired. Following firing, the staples 14 will form a enlarged anastomotic ring in the connected lumen sections 10 and 12 with the knife portions 110 trimming off the inner diameter of the lumen sections 10 and 12 secured to the stapler 100 with the purse strings. The head 90 and anvil 120 can be returned to the retracted position following the loosening of the clamped sections to allow the removal of the stapler 100.

The present invention operates essentially the same as existing end to end anastomotic devices with a significantly enlarged anastomosis ring. Specifically, the area at the anastomosis site is not decreased or reduced relative to the normal diameter of the anastomized sections.

Figure 7A:
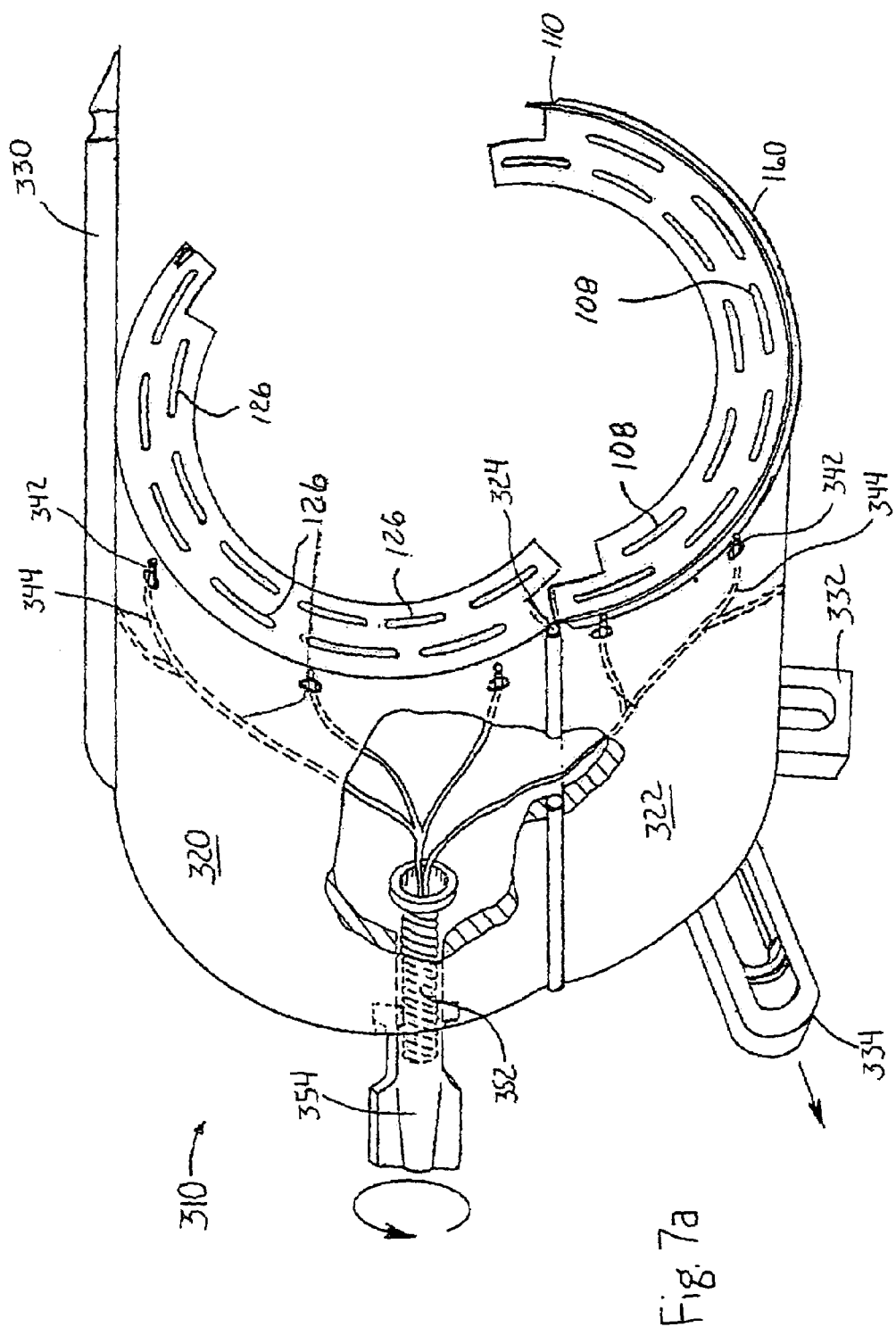
FIG. 7a is a perspective view partially in section of a first half of an extraluminal end to end surgical stapler according to the present invention.
Figure 7B:
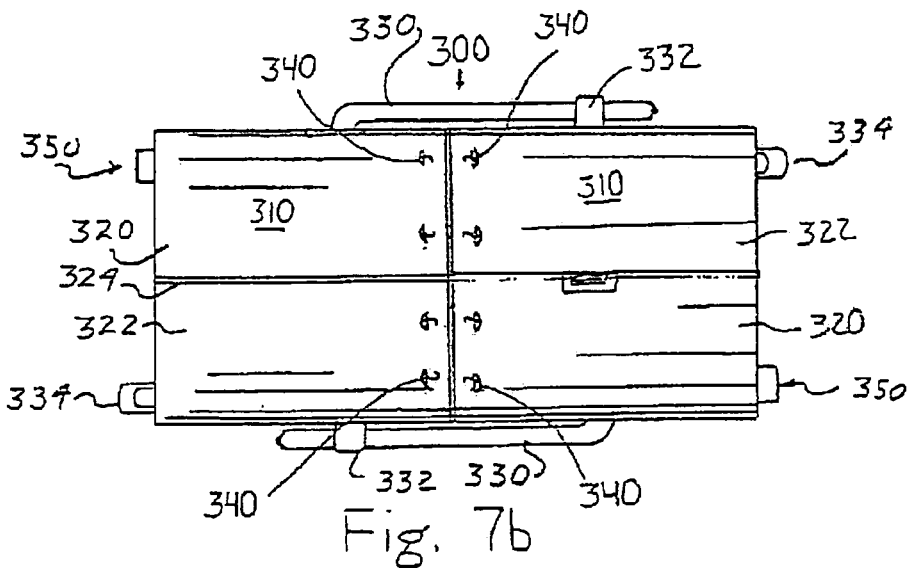

FIGS. 7a and 7b illustrate an extraluminal end to end surgical stapler 300 according to the present invention. The stapler 300 is intended to form anastomized lumen sections with an externally located anastomosis ring relative to the lumen sections 10 and 12 illustrated in FIG. 1c.

The stapler 300 according to the present invention includes two separate stapling units 310, with each stapling unit 310 generally including two semi-circular sections 320, 322 hinged together by a hinge 324 extending along the length of the stapling unit. One stapling unit 310 is shown in FIG. 7a. In a preferred embodiment of the present invention, one half of each stapling unit 310 is formed as an anvil 320 having conventionally positioned staple receiving grooves 126 staggered thereon. The other semi-circular section 322 includes staples 14 and knife portion 110. The section 322 includes a series of staple receiving slots 108 for the staples 14 and a knife receiving groove 160 with the semi-circular knife portion 110 received in the groove 160. The staples 14 and knife portions 110 can be fired with a firing mechanism essentially the same as illustrated in the segments 102, 104 shown in FIGS. 5a–5g and therefore need not be discussed in detail. One difference is that the groove 160 is at the radially outer edge rather than on the radially inner edge. A firing rod 172 is attached to a base plate 162, not shown, and can be directly connected through the housing 333 to a linkage (not shown) associated with a firing trigger. The anvil and head sections 320 and 322 shown in FIG. 7a form one entire stapling unit 310 which forms one-half of the stapler 300. Another identical stapling unit 310 would be attached in an opposite face to face engagement (as shown in FIG. 7b.). Each staple and knife firing head section 322 is associated with the anvil section 320 of the opposite stapling unit 310, and vice versa. In other words, half of the staples 14 of the complete anastomosis ring would be fired from one direction and the other half would be fired by the other stapling unit 310 in the opposite direction. Each stapling unit 310 includes alignment mechanisms for combining with the opposite stapling unit 310 to complete the pair of the stapler 300. The alignment mechanisms can be easily constructed as a rod 330 extending from one section 320 which is received in a locking projection 332 formed on an opposite section 322. This construction will allow for easy alignment and attachment of the opposed stapling units 310.

Another key aspect of the present invention is a tissue holding mechanism for pulling the tissue of the lumen sections 10 or 12 to be attached over the operating face of the stapling units 310. As will be appreciated by those of ordinary skill in the art, with such an extraluminal stapler 300 as disclosed, purse strings would not be very efficient for positioning of the lumen sections 10 and 12 to be attached on the stapler 300. To accomplish the positioning of the tissue, each stapling unit 310 includes a plurality of tissue retraction members 340 spaced around the periphery of each stapling unit 310. The tissue retraction members 340 are in the form of hooks 342 formed at the end of cables 344 at circumferentially spaced locations. The cables 344 extend along grooves formed in the body 190 back to a central controlling structure 350 in the form of an axially movable stud 352 controlled by a rotatable controller 354 journaled to the body 190. It should be evident that rotation of the controller 354 will axially move the stud 352 allowing the cables 344 to be pulled out of the body 190 or retracted back into the body 190. With this construction, the hooks 342 can be pulled out and clipped onto the tissues at circumferentially spaced locations around the lumen section 10 or 12 and the controller 354 can be rotated to pull the hooks 342 and the associated tissue back until tissue is surrounding the operating face of the one stapling unit 310.

Figure 8A:
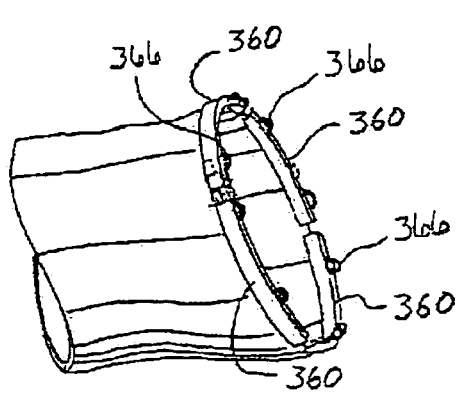
FIG. 8a is a perspective view of a lumen section to be anastomized utilizing flexible clips associated with the surgical stapler illustrated in FIGS. 7a and 7b.
Figure 8B:
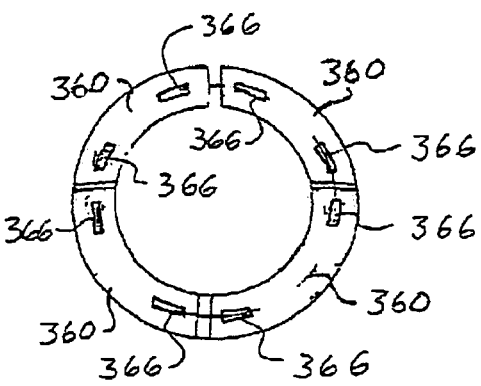
Figure 8C:
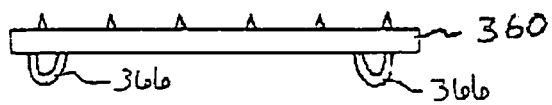
FIG. 8c is a side view of the clips utilized in FIGS. 8a and 8b in the open position.
Figure 8D:
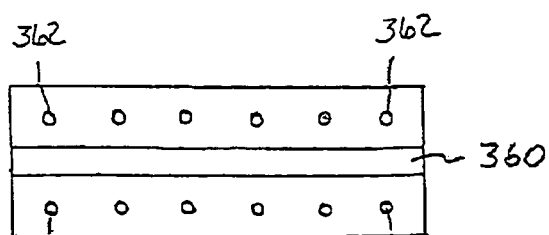
FIG. 8d is a plan view with the clips in the open position of the clip illustrated in FIG. 8c.
Figure 8E:
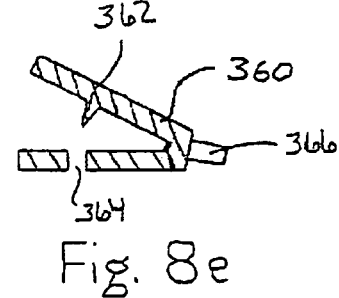
FIG. 8e is a cross-section of the clips illustrated in FIGS. 8c and 8d with the clip in a partially closed position.

It is anticipated that certain tissue may not be efficiently stretched by a hook 342 attached at a single location (i.e., it may tear). To eliminate this, the present invention contemplates flexible clips 360 attached to the edge of the lumen sections 10 or 12 such as shown in FIGS. 8a–8e. The clips 360 are formed of a flexible hinged strip of material that can be secured around the edge of the resected lumen section. As shown in FIGS. 8c–8e, one simple construction for forming the clips 360 is to provide a series of piercing projections 362 on one side of the clip 360 which engage in snap fit receiving holes 364 on the opposite side of the clips 360 such that the clips 360 can be easily press fit in position in a fast and secure manner. The clips 360 include a pair of eyelets 366 at spaced locations thereon with the eyelets 366 forming a connection point for the associated hooks 342 of each stapling unit 310. The purpose of the clips 360 is to provide rigidity to the end of the lumen sections 10 or 12 being pulled and to distribute the stresses of pulling on the lumen section 10 or 12 across a greater area to avoid damaging the lumen section 10 or 12 and to easily pull the lumen section 10 or 12 into the extended position around the face of a stapling unit 310.

In operation, the extraluminal stapler 300 illustrated in FIGS. 7a and 7b operates as follows. After the resected portion of the lumen is removed and the two remaining lumen sections 10 and 12 are to be attached, two separate stapling units 310 forming a combined stapler 300 are attached with one unit 310 around each lumen section 10 or 12. Clips 360 are positioned around the edge of each lumen section 10 or 12 as illustrated in FIG. 8a and the controller 354 is rotated to release the cables 344 to allow enough slack to attach the hooks 342 to the eyelets 366 of the clips 360. Once the eyelets 366 are attached to the associated clips 360, the controller 354 can be rotated retract the cables 344, the hooks 342 and the associate clips 360 properly positioning the lumen section 10 or 12 over the operating face of the associated stapling unit 310. Following this, the stapler 300 of the present invention allows for visual inspection to assure that the lumen is properly positioned prior to snapping the two stapling units 310 together using the alignment mechanisms formed by rod 330 and locking projection 332. The alignment mechanisms will preferably snap or hold the two stapling units 310 together at a position sufficient for firing. It will be understood that an appropriate safety mechanism can be associated so that the staples 14 could not be fired until the opposing stapling unit 310 is secured thereto. Once the opposing stapling unit 310 is secured, the staplers 14 on both halves (i.e., in both stapling units 310) can be fired performing the anastomosis. Following this, the two stapling units 310 can be removed from each other and each independently opened and the external stapler is removed from the anastomized lumen.

Figure 9:
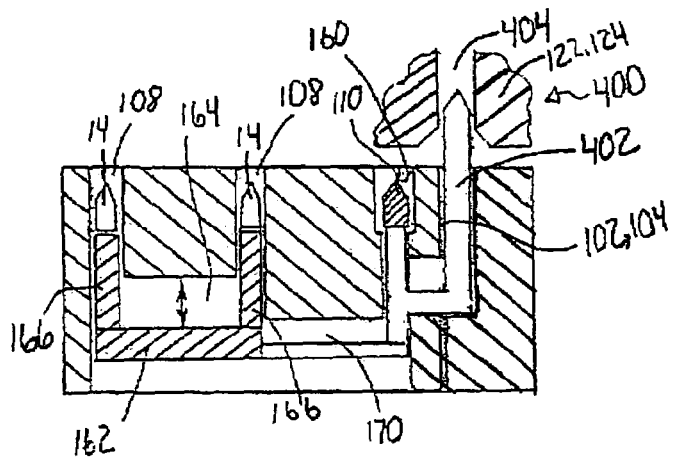
FIG. 9 is a sectional schematic view of an alignment mechanism for use in a stapler of the present invention.

The use of an alignment mechanism for aligning the head and anvil portions of EEA staplers such as shown in staplers units 310 would also be beneficial for internal EEA staplers such as shown in FIGS. 6a–e. The present invention contemplates an alignment mechanism 400 associated with such an EEA stapler as schematically shown in FIG. 9. The alignment mechanism 400 essentially includes a plurality of locking pins 402 associated with each head segment 102 and 104. The locking pins 402 are received in mating holes 404 on the associated anvil segments 122 or 124. The holes 404 preferably have a beveled outer surface to receive and guide the locking pins 402 into the holes 404. With the locking pins 402 received in the holes 404 the head and anvil portion of the stapler will be properly aligned. The pins 402 may be moved by the same firing mechanism as the staples and the blade as shown in FIG. 9. A separate pin movement mechanism may also be provided. It is important that the pins 402 be engaged with the holes 404 prior to the engagement of the staples or the knife blade with the lumen tissue, since it is the pins 402 which are assuring the alignment of the head and anvil portions. Consequently where a single firing mechanism is utilized the pins 402 should be axially ahead of the staple and knife blade portions as shown in an exaggerated fashion in FIG. 9. Another feature of the present invention is to offset the anvil segments and the head segments such that the pins 402 of each head segment will lock the head segment to two corresponding overlapping anvil segments. This will effectively interlock all of the head and anvil segments during firing to provide a conventional solid hoop structure for these components during the staple firing and knife trimming operation. It should be apparent that this alignment mechanism 400 will be applicable to EEA devices that do not have separate head and anvil segments.

Various modifications to this invention are contemplated within the scope of the present invention. For example, additional clamping between the stapling units 310 may be accomplished by having the alignment mechanism on each stapling unit 310 (i.e., the rod 330 and locking projection 332) be independently axially movable such that when the two stapling units 310 are clamped together, axial movement of the associated alignment mechanism will move the two stapling units 310 closer together (or farther apart) to accommodate the desired clamping. Another modification of the present invention would be to connect the firing of one stapling unit 310 to the firing of the other stapling unit 310, such as through the associated alignment mechanism, so that the user need only pull one trigger 334 to fire the two halves of staples 14. Another modification to the present invention would be to form the separate units as having an entire array of staples on one stapling unit 310 and two anvil portions on the other stapling unit 310. However, the present invention simplifies the manufacturing of the stapler 300 by forming an entire stapler 300 of two identical stapling units 310. Regardless, these and other modifications make it clear that various changes to the present invention can be accomplished without departing from the spirit and scope thereof. For example, the staples 14 could be replaced with another type of fastener. The described embodiments are merely intended to be illustrative of the present invention and not restrictive thereof. The scope of the present invention is intended to be defined by the appended claims and equivalents thereof.

What is claimed is:

1. A surgical anastomotic fastener array comprising a plurality of fasteners each having at least one tissue piercing element, wherein the fasteners are aligned in an annular array of a first diameter prior to anastomosis and are configured to move in a radial direction to form an annular array of a second diameter different from the first diameter, and a mechanism for accommodating radial movement of the annular array of fasteners.

2. The fastener array of claim 1 wherein the plurality of fasteners are staples, each staple having two tissue piercing elements, and the mechanism for accommodating radial movement expands the diameter of the annular array from the first diameter to second diameter prior to anastomosis.

3. The fastener array of claim 1 further including a second annular array of fasteners aligned coaxially with the fasteners of the first annular array of fasteners in an initial diameter prior to anastomosis and designed to expand to form an annular array of fasteners of a diameter larger than the initial diameter.

4. The fastener array of claim 1 wherein the fastener array is expanded to the second larger diameter at time of firing of the fasteners to form an anastomotic ring.

5. The fastener array of claim 1 wherein the array is in an anastomotic stapler for end to end anastomosis forming an anastomotic ring, and wherein the plurality of fasteners are staples formed in a pair of offset annular arrays of staples to couple the end of a first lumen section to the end of a second lumen section, said stapler including:
a head portion including a stapling mechanism wherein the head portion comprises a plurality of wedge-shaped arc segments that align to form an annular head, each segment having at least one staple therein and wherein each arc segment has a separate, independent firing mechanism for firing the staples of that segment; and
an anvil portion aligned with the segments of the head portion.

6. The fastener array of claim 5, wherein each arc segment has an arcuate knife portion that will overlap with knife portions of adjacent arc segments when the staples are fired.

7. The fastener array of claim 6, wherein each arc segment has a separate, independent knife actuating mechanism.

8. The fastener array of claim 5, wherein the plurality of arc-shaped segments move rotationally from an overlapped formation in a retracted position to align in an expanded position forming the annular head.

* * * * *